(12) United States Patent
Fujii et al.

(10) Patent No.: US 9,814,683 B2
(45) Date of Patent: Nov. 14, 2017

(54) SHELL-FORMING COMPOSITIONS FOR SOFT CAPSULES AND SOFT CAPSULES

(71) Applicant: R.P. Scherer Technologies, LLC, Las Vegas, NV (US)

(72) Inventors: Takuma Fujii, Kakegawa (JP); Toshikazu Okayama, Kakegawa (JP); Michihiro Kimata, Kakegawa (JP); Yoshiaki Hanayama, Kakegawa (JP); Miyako Takahashi, Kakegawa (JP)

(73) Assignee: R.P. SCHERER TECHNOLOGIES, LLC, Las Vegas, NV (US)

( * ) Notice: Subject to any disclaimer, the term of this patent is extended or adjusted under 35 U.S.C. 154(b) by 51 days.

(21) Appl. No.: 14/392,343

(22) PCT Filed: Jun. 24, 2014

(86) PCT No.: PCT/US2014/043814
§ 371 (c)(1),
(2) Date: Dec. 24, 2015

(87) PCT Pub. No.: WO2014/209964
PCT Pub. Date: Dec. 31, 2014

(65) Prior Publication Data
US 2016/0271069 A1  Sep. 22, 2016

(30) Foreign Application Priority Data
Jun. 25, 2013  (JP) ................. 2013-132728

(51) Int. Cl.
*A61K 9/48* (2006.01)
(52) U.S. Cl.
CPC .......... *A61K 9/4816* (2013.01); *A61K 9/4808* (2013.01)
(58) Field of Classification Search
CPC ........................... A61K 9/4816; A61K 9/4808
See application file for complete search history.

(56) References Cited

U.S. PATENT DOCUMENTS

| | | | |
|---|---|---|---|
| 6,375,981 B1 | 4/2002 | Gilleland et al. | |
| 2003/0138482 A1 | 7/2003 | Fonkwe et al. | |
| 2004/0052839 A1* | 3/2004 | Archibald | A61K 9/4891 424/452 |
| 2005/0019295 A1 | 1/2005 | Ballard et al. | |
| 2005/0152968 A1* | 7/2005 | Brophy | A61K 9/1075 424/451 |
| 2006/0099246 A1 | 5/2006 | Tanner et al. | |
| 2008/0138402 A1 | 6/2008 | Li et al. | |
| 2011/0171281 A1 | 7/2011 | Cao | |
| 2012/0058181 A1* | 3/2012 | Currie | A61K 9/0036 424/456 |

FOREIGN PATENT DOCUMENTS

| | | |
|---|---|---|
| EP | 1105107 | 1/2001 |
| JP | 2010180159 A | 8/2010 |
| JP | 2011012003 A | 1/2011 |
| JP | 2011153147 | 8/2011 |
| WO | WO2012018329 A1 | 2/2012 |

OTHER PUBLICATIONS

International Search Report and Written Opinion; dated Nov. 5, 2014 for PCT Application No. PCT/US2014/043814.
Japanese Office Action; dated Jan. 19, 2015 for JP Application No. JP2013-132728.
Shibata, I., "Contributing to the society in our role as specialists with the application of many products to various fields, starting with water for medical purposes," Research and study report of vegetable-derived capsules, PHARM TECH Japan, 2004, vol. 20, No. 10, 2011-2014.
European Search Report; dated Feb. 6, 2016 for EP Application No. EP14816696.0.

* cited by examiner

*Primary Examiner* — Jianfeng Song
(74) *Attorney, Agent, or Firm* — Mendelsohn Dunleavy, P.C.

(57) ABSTRACT

A shell-forming composition for a soft capsule comprising a non-gelatin component as the chief component, wherein the shell-forming composition is able to inhibit a decrease in physical strength (breaking strength) of the capsule when a phospholipid-containing oil with a phospholipid concentration of 20% or more by mass is used as the core of the capsule. The shell-forming composition for the soft capsule comprises (A) starch and/or dextrin, (B) a gelatinizer, (C) glycerin and (D) sorbitol, and the mass ratio of (C) glycerin: (D) sorbitol ranges from 100:30 to 100:120.

19 Claims, No Drawings

SHELL-FORMING COMPOSITIONS FOR SOFT CAPSULES AND SOFT CAPSULES

TECHNICAL FIELD

The present invention relates to a shell-forming composition for soft capsules suitable for coating a capsule core containing a high phospholipid-containing oil. The invention also relates to a soft capsule and a breaking strength decrease inhibitor for a soft capsule formed using said composition.

BACKGROUND

Soft capsules are widely used in fields such as medical and pharmaceutical products and foods. Gelatin is widely used as the chief component of the shell of such soft capsules, and gelatin is produced mainly from bovine bone or porcine skin. However, there is a problem that vegetarians, Muslims who prohibit porcine consumption, and Hindus who regard the cow as sacred, are not able to take or eat capsules containing gelatin of bovine or porcine origin.

Furthermore, uncertainty remains regarding the safety of such capsules from bovine spongiform encephalopathy in gelatin produced from bovine bone. Also, non-bovine or non-porcine gelatin not only is unable to provide the strength required for capsules but also has a problem that it has a lower cost performance and costs more when compared to bovine or porcine gelatin.

Under these circumstances, botanical capsules obtained by forming soft capsules without using gelatin are being proposed (for example, patent documents 1-4) listed below. These botanical capsules are produced from components of botanical origin and therefore do not raise the issues mentioned above that result from using gelatin of bovine or porcine origin.

Patent document 1: No. 2003-504326
Patent document 2: No. 2005-176744
Patent document 3: No. 2008-519075
Patent document 4: No. 2010-180159

SUMMARY OF THE INVENTION

Problems to be Solved by the Invention

Since phospholipids are effective in maintaining human health, the present inventors attempted to provide a supplement in which oils containing a high concentration of phospholipids are encapsulated. The present inventors perceived that a problem of a decrease in physical strength (breaking strength) occurs when botanical soft capsules are filled with such high phospholipid-containing oils.

An object of the present invention is to provide a shell-forming composition for a soft capsule comprising a non-gelatin component as the chief component, wherein the a shell-forming composition for the soft capsule is able to inhibit a decrease in physical strength (breaking strength) of the capsule which would otherwise occur when a phospholipid-containing oil, having, for example, a phospholipid concentration of 20% or more by mass, is used in a core of the capsule.

Another object of the present invention is to provide a soft capsule comprising a shell formed by the above-described shell-forming composition.

Another object of the present invention is to provide a breaking strength decrease inhibitor for a soft capsule which can accommodate a core containing a phospholipid-containing oil, e.g. with a phospholipid concentration of 20% or more by mass.

Means for Solving the Problem

The present invention was made based on the finding that in shell-forming compositions for soft capsules comprising a non-gelatin component as the chief component the problems described above cannot be solved by using glycerin or sorbitol alone. However, the problems described above can be solved when (C) glycerin and (D) sorbitol are employed together at a specific mass ratio.

Namely, the present invention provides a shell-forming composition for a soft capsule for accommodating a core containing a phospholipid-containing oil, for example with a phospholipid concentration of 20% or more by mass, wherein the shell-forming composition is characterized by comprising: (A) starch and/or dextrin, (B) gelatinizer, (C) glycerin and (D) sorbitol and having a mass ratio of (C) glycerin to (D) sorbitol ranging from 100:30 to 100:120 of glycerin to sorbitol.

The present invention also provides a soft capsule comprising a shell formed by a shell-forming composition for a soft capsule as described above and a capsule core containing a phospholipid-containing oil with a phospholipid concentration of 20% or more by mass within said shell.

The present invention also provides a breaking strength decrease inhibitor for soft capsules accommodating a core containing a phospholipid-containing oil with a phospholipid concentration of 20% or more by mass, wherein said breaking strength decrease inhibitor comprises component (C) glycerin and component (D) sorbitol at a mass ratio ranging of from 100:30 to 100:120 of glycerin to sorbitol.

MODES FOR CARRYING OUT THE INVENTION

Component (A) of the shell-forming composition for the soft capsule of the present invention is starch, dextrin, or a combination thereof. Here, examples of a starch include one or a mixture of two or more types of starches of corn, various kinds of barley and wheat, various kinds of tubers such as potatoes and beans, and various kinds of modified starch and the like. Among these, one or a combination of two or more types selected from a group consisting of corn starch, hydroxypropyl starch, acid-treated starch and dextrin are preferred, and hydroxypropyl starch and acid-decomposed waxy corn starch are more preferred. The amount of the component (A) for soft capsules is preferably 10-60% by mass of the shell-forming composition based on the dry weight of the composition not including water and more preferably 25-60% by mass of the shell-forming composition based on the dry weight of the composition.

Examples of the gelatinizer, the (B) component of the shell-forming composition for a soft capsule of the present invention, include one or a mixture of two or more types of gelatinizers selected from carrageenans (iota-carrageenan, kappa-carrageenan, lambda-carrageenan), agar, gum arabic, gellan gum, native gellan gum, pullulan, pectin, glucomannan, locust bean gum, guar gum, cellulose, konjac gum, furcellaran, tara gum, alginate and tamarind gum. Among these, one or a mixture of two or more types selected from carrageenans (iota-carrageenan, kappa-carrageenan, lambda-carrageenan), locust bean gum, pullulan, native gellan gum, or deacylated gellan gum are preferred. Above all, iota-carrageenan alone, kappa-carrageenan alone, lambda-carrageenan alone, or combinations thereof are particularly preferred.

The amount of the gelatinizer, the component (B) within the shell-forming composition (based on the dry weight or compositions not including water) for the soft capsule of the present invention, is preferably 8-30% by mass and more preferably 10-24% by mass.

The present invention is characterized by using (C) glycerin and (D) sorbitol as the plasticizer at a mass ratio ranging from 100:30 to 100:120 and more preferably at a mass ratio ranging from 100:40 to 100:70, glycerol to sorbitol.

The total amount of the components (C) and (D) within the film-forming composition (based on the dry weight or compositions not including water) for soft capsules of the present invention is preferably 5-65% by weight, more preferably 10-60% by weight, and even more preferably 15-60% by weight. Plasticizers other than the components (C) and (D), such as propylene glycol and polyethylene glycol, can be used at the same time, although this is not preferable.

A buffer component (E) may be included in the film-forming compositions for soft capsules of the present invention. Examples of a buffer include sodium salts, potassium salts, calcium salts and the like, with sodium phosphate being preferable. Buffers that function as pH buffers are also preferred.

The amount of the buffer of component (E) within the film-forming composition (based on the dry weight or compositions not including water) included in the soft capsule of the present invention, is preferably 0.2-5% by mass and more preferably 1-4% by mass.

Using carrageenan as the gelatinizer of component (B) is preferable because it can avoid carrageenan gelatinization from requiring the use of buffers such as sodium salt, potassium salt and calcium salt that are generally required. In this case, using the component (A) and (B) the gelatinizer are used at a mass ratio of A:B ranging from 1:1 to 4:1.

Coloring agents such as pigments and paint, flavoring agents, preservatives, and the like may also be included in the film-forming composition for the soft capsule of the present invention. It is preferably not to use gelatin in the soft capsule formulations.

When forming a shell for a soft capsule using the film-forming composition for the soft capsule of the present invention, 40-130 parts by mass of water may be added to and mixed with 100 parts by mass of the shell-forming compositions for the soft capsules of the present invention. The coating may be formed to a thickness of 0.1-1.0 mm using any conventional method. A seamless capsule can be also formed using a shell-forming composition for the soft capsule of the present invention.

The shell-forming compositions for the soft capsule of the present invention are particularly suitable for accommodating a core containing a phospholipid-containing oil with a phospholipid concentration of 20% or more by mass. Examples of such phospholipid-containing oils with a phospholipid concentration of 20% or more by mass include lecithin, high lecithin-containing oils, krill oil and the like.

These oils can be diluted with an oil diluent for use. Examples of such an oil diluent include various kinds of edible oils such as soybean oil, rapeseed oil, palm oil, safflower oil, perilla oil, linseed oil, olive oil, rice oil and sesame oil, DHA-containing fish oil, EPA-containing fish oil and functional fats such as squalene. Among these, ones that are in liquid form at room temperature are preferable.

In the present invention, an oil having a phospholipid concentration of 30% or more by mass is preferable. A phospholipid concentration of 30-60% by mass is more preferable, and a phospholipid concentration of 30-50% by mass is particularly preferred.

The breaking strength decrease inhibitor for a soft capsule accommodating the core of the present invention, all of the foregoing statements such as the preferred range of the (C) glycerin:(D) sorbitol ratio and the preferred phospholipid content in the high phospholipid-containing oil will apply.

The present invention will be further explained below through the following examples.

EXAMPLES

Example 1

Materials were mixed in the amounts shown in Table 1 and melted by application of heat. The melted material was spread to a uniform thickness using an appropriate container, and three types of films (thickness 500 μm, length 5 mm, width 10 mm) for soft capsules, whose plasticizer is glycerin alone, sorbitol alone, or a mixture of glycerin and sorbitol (100:50), were produced. Each film was immersed in hill oil (okiami oil: Aker BioMarine) whose phospholipid concentration was 40% by mass, and changes in the hardness of the film piece after one week were tested by bending the film piece with fingers. A summary of the results is shown in Table 1, wherein the S:G mixture corresponds to the present invention.

TABLE 1

|  | glycerin (G) alone | sorbitol (S) alone | S:G mixture |
| --- | --- | --- | --- |
| S:G mass ratio | 0:100 | 100:0 | 50:100 |
| glycerin | 20.9 | 0 | 13.9 |
| sorbitol*1 | 0 | 20.9 | 7.0 |
| processed starch*2 | 21.5 | 21.5 | 21.5 |
| carrageenan | 7.6 | 7.6 | 7.6 |
| Na phosphate | 0.7 | 0.7 | 0.7 |
| water | 49.3 | 49.3 | 49.3 |

*Blending amounts in Table 1 are in parts by mass.
*1Sorbit L-70 by Mitsubishi Shoji Foodtech Co., Ltd was used as the sorbitol. Since the sorbitol content of Sorbit L-70 is 70% by mass, the recipe shows the amount of sorbitol instead of the amount of Sorbit L-70.
*2hydroxypropyl starch Hardness was tested by bending the film. The suitability of the film for the coating of a soft capsule was also examined. Changes in the hardness of the film piece after one week are summarized and shown in Table 2.

TABLE 2

|  | glycerin (G) alone | sorbitol (S) alone | S:G mixture |
| --- | --- | --- | --- |
| hardness | hard ( ) | very hard ( ) | soft and suitable for soft capsules (⊙) |

The results given above in Table 2 show that films for soft capsules in which sorbitol (S) and glycerin (G) are used at a ratio of 50:100 do not harden after one week of immersion in krill oil whose phospholipid concentration is 40% by mass and therefore remain soft and suitable for a soft capsule.

Example 2

The mass ratio of sorbitol:glycerin was varied from 21:100 to 210:100 according to the blending examples shown in Table 1 and films (thickness 500 μm) for soft capsules were prepared, and film pieces with a length of 5 mm and a width of 10 mm were produced. The film pieces were immersed in krill oil whose phospholipid concentration was 40% by mass, and changes in the hardness of the film piece after one week were tested by bending the film piece with fingers and were evaluated based on the criteria below. The results are summarized in Table 3, wherein the sorbitol:glycerin ratios of 100:35 to 100:84 correspond to compositions of the present invention.

The feel to the finger was evaluated based on the criteria below.

: hard and breakable
○: flexible but somewhat hard (35, 42) or soft (77, 84)
⊙: the hardness and flexibility are most suitable for the coating of a soft capsule The results are summarized in Table 3.

TABLE 3

| | sorbitol:glycerin mass ratio | | | | | | | | |
|---|---|---|---|---|---|---|---|---|---|
| | 21*[1] | 28 | 35 | 42 | 54 | 63 | 70 | 77 | 84 | 140 | 210 |
| changes in the hardness of the coating piece | | | ○ | ○ | ⊙ | ⊙ | ⊙ | ○ | ○ | Δ | Δ |

21*[1] in Table 3 means a ratio of sorbitol:glycerin of 21:100. In each case, the value 100 for glycerin is not shown in Table 3 but is assumed.

When the sorbitol:glycerin mass ratio was 100:21 or 100:28, the film piece was found to harden after being immersed in krill oil. It was found that the coating softens when the amount of sorbitol is higher than 70 parts by mass per 100 parts by mass of glycerin, and significantly softer when the amount of sorbitol is higher than 140 parts by mass per 100 parts by mass of glycerin.

Examples 3-6

Melted coating material that can be formed into capsules was produced by mixing and heat-melting the components shown in Table 4. Subsequently, hill oil whose phospholipid concentration was 40% by mass was used as a capsule fill, and soft capsules with a major axis of approximately 14.3 mm and a minor axis of approximately 9.2 mm were prepared using a roll die-type encapsulation machine. Furthermore, the breaking strength of the soft capsules was determined by measuring the weight of the load at the point when the capsule ruptured using a Kiya-style rigidity tester (model 1600-E: Fujiwara Scientific Company Co., Ltd).

TABLE 4

| | Comparative Example 1 | Example 3 | Example 4 | Example 5 | Example 6 |
|---|---|---|---|---|---|
| sorbitol/glycerin mass ratio | 0:100 | 30:100 | 54:100 | 70:100 | 120:100 |
| glycerin | 18.3 | 13.5 | 13.5 | 13.5 | 13.5 |
| sorbitol*1 | 0 | 4.1 | 7.4 | 9.5 | 16.2 |
| processed starch*2 | 23.5 | 21.5 | 21.5 | 21.5 | 21.5 |
| carrageenan | 7.6 | 7.6 | 7.6 | 7.6 | 7.6 |
| Na phospate | 0.7 | 0.7 | 0.7 | 0.7 | 0.7 |
| water | 49.9 | 52.6 | 49.3 | 47.2 | 40.5 |
| Breaking strength (kg)*3 | 13.9 | 18.4 | 24.7 | 23.8 | 17.5 |

*Blending amounts in Table 4 are in mass parts.
*[1]Sorbit L-70 by Mitsubishi Shoji Foodtech Co., Ltd was used as the sorbitol. Since the sorbitol content of Sorbit L-70 is 70% by mass, the recipe shows the amount of sorbitol instead of the amount of Sorbit L-70.
*[2]hydroxypropyl starch
*[3]average of ten tests Decreases in the breaking strength of soft capsules filled with hill oil whose phospholipid concentration was 40% by mass are shown to be inhibited due by the present invention.

Time-dependent changes in the breaking strength of the soft capsules of Example 4 were measured, and the results are shown in Table 5.

TABLE 5

(Time-dependent changes in the breaking strength)
Results from the rapture test

| | starting point | 2 months later | 4 months later | 6 months later |
|---|---|---|---|---|
| Example 4 | 24.7 kg | 27.8 kg | 25.2 kg | 25.6 kg |

According to these results, soft capsules made in accordance with the invention and filled with a phospholipid oil having a high phospholipid concentration were shown to maintain a good breaking strength even after 6 months of storage (Example 4).

The invention claimed is:

1. A shell-forming composition for a soft capsule for accommodating a core containing a phospholipid-containing oil with a phospholipid concentration of 20% or more by mass, comprising:
   (A) starch and/or dextrin;
   (B) gelatinizer;
   (C) glycerin; and
   (D) sorbitol;
   wherein the mass ratio of (C) glycerin:(D) sorbitol ranges from 100:54 to 100.70.

2. The composition of claim 1, wherein said component (A) starch and/or dextrin comprises one or two or more starches selected from the group consisting of corn starch, hydroxypropyl starch, acid-treated starch and dextrin.

3. The composition of claim 2, wherein said component (A) comprises hydroxypropyl starch.

4. The composition of claim 1, wherein said gelatinizer (B) comprises one or two or more gelatinizers selected from the group consisting of carrageenan, locust bean gum, native gellan gum and deacylated gellan gum.

5. The composition of claim 1, further comprising (E) a buffer.

6. The composition of claim 5, wherein said buffer (E) is a sodium salt, a potassium salt, or a calcium salt.

7. The composition of claim 1, wherein said composition does not comprise a buffer.

8. A soft capsule comprising:
   a shell formed by a composition of claim 1; and
   a capsule core containing a phospholipid-containing oil with a phospholipid concentration of 20% or more by mass located within said shell.

9. The composition of claim 2, wherein said gelatinizer (B) comprises one or two or more gelatinizers selected from the group consisting of carrageenan, locust bean gum, native gellan gum and deacylated gellan gum.

10. The composition of claim 3, wherein said gelatinizer (B) comprises one or two or more gelatinizers selected from the group consisting of carrageenan, locust bean gum, native gellan gum and deacylated gellan gum.

11. The composition of claim 2, further comprising (E) a buffer.

12. The composition of claim 3, further comprising (E) a buffer.

13. The composition of claim 4, further comprising (E) a buffer.

14. The soft capsule of claim 8, wherein said shell component (A) starch and/or dextrin comprises one or two or more starch selected from the group consisting of corn starch, hydroxypropyl starch, acid-treated starch and dextrin.

15. The soft capsule of claim 8, wherein said shell component (A) comprises hydroxypropyl starch.

16. The soft capsule of claim 8, wherein said gelatinizer (B) comprises one or two or more gelatinizers selected from the group consisting of carrageenan, locust bean gum, native gellan gum and deacylated gellan gum.

17. The soft capsule of claim 8, wherein said shell further comprises (E) a buffer.

18. The soft capsule of claim 17, wherein said buffer (E) is a sodium salt, a potassium salt, or a calcium salt.

19. The soft capsule of claim 8, wherein said shell composition does not comprise a buffer.

* * * * *